(12) United States Patent
Shen et al.

(10) Patent No.: US 8,241,570 B1
(45) Date of Patent: Aug. 14, 2012

(54) FLOW CELL DEVICE

(75) Inventors: Chi-Yen Shen, Kaohsiung (TW);
Jian-Jhong Chen, Kaohsiung (TW);
Yu-Fong Huang, Kaohsiung (TW)

(73) Assignee: I Shou University, Kaohsiung (TW)

( * ) Notice: Subject to any disclaimer, the term of this patent is extended or adjusted under 35 U.S.C. 154(b) by 0 days.

(21) Appl. No.: 13/020,177

(22) Filed: Feb. 3, 2011

(51) Int. Cl.
*G01N 15/06* (2006.01)

(52) U.S. Cl. .................................... 422/68.1

(58) Field of Classification Search ................ 422/68.1
See application file for complete search history.

(56) References Cited

U.S. PATENT DOCUMENTS

| | | | | |
|---|---|---|---|---|
| 3,505,024 A | * | 4/1970 | Ohms et al. | 422/51 |
| 3,728,032 A | * | 4/1973 | Noll | 356/246 |
| 3,946,239 A | * | 3/1976 | Salzman et al. | 250/461.2 |
| 4,829,003 A | * | 5/1989 | Arney, Jr. | 435/287.1 |
| 5,344,545 A | * | 9/1994 | Tsukada et al. | 204/415 |
| 5,433,019 A | * | 7/1995 | Fu et al. | 34/381 |
| 5,460,945 A | * | 10/1995 | Springer et al. | 435/7.24 |
| 5,466,416 A | * | 11/1995 | Ghaed et al. | 422/52 |
| 6,188,813 B1 | * | 2/2001 | Dourdeville et al. | 385/12 |
| 6,309,532 B1 | * | 10/2001 | Tran et al. | 205/687 |
| 7,998,436 B2 | * | 8/2011 | Pollack et al. | 422/509 |

* cited by examiner

*Primary Examiner* — Bobby Ramdhanie
(74) *Attorney, Agent, or Firm* — Kilpatrick Townsend & Stockton LLP

(57) ABSTRACT

A flow cell device is formed with: a plurality of cell recess portions adapted to cooperate with a plurality of sensor devices to confine a plurality of sample receiving space for receiving a liquid sample, respectively; a plurality of pairs of first and second guiding channels, each pair being in fluid communication with a respective one of the cell recess portions; a number of connecting recess portions each fluidly communicating the first and second guiding channels that respectively extend to a corresponding pair of the cell recess portions such that the liquid sample is able to flow through the sample receiving spaces sequentially; and inlet and outlet channels in fluid communication with the first and second guiding channels that respectively extend to a first one and a last one of the cell recess portions for introducing and discharging the liquid sample into and from the flow cell device, respectively.

12 Claims, 3 Drawing Sheets

FLOW CELL DEVICE

BACKGROUND OF THE INVENTION

1. Field of the Invention

The present invention relates to a flow cell device, more particularly to a flow cell device suitable for determining concentration of a predetermined osteoarthritis biomarker in a liquid sample.

2. Description of the Related Art

Conventional diagnosis of orthopedic diseases is often based upon subjective descriptions of symptoms as experienced by a person suspected of having orthopedic diseases, and results obtained from invasive examination techniques, such as X-ray and MRI, which may be very time-consuming.

In recent years, owing to rapid development of molecular biology, pathological variations and biological mechanisms of various diseases may now be investigated and studied at a molecular level, which is very helpful in early detection of the diseases, where symptoms of the diseases are often subtle. Taking osteoarthritis as an example, a sensor device that detects concentration of an osteoarthritis biomarker in a liquid sample and generates an electrical signal accordingly is often used in detection of osteoarthritis. However, since the liquid sample is dropped onto a sample sensing surface of the sensor device using a dropper, the height from which the liquid sample is dropped and the region of the sample sensing surface onto which the liquid sample is dropped may be different for each measurement, which may compromise reliability of a measurement result thus obtained.

SUMMARY OF THE INVENTION

Therefore, an object of the present invention is to provide a flow cell device capable of alleviating the aforesaid drawbacks of the prior art.

Accordingly, a flow cell device of the present invention is adapted for use with a plurality of sensor devices to detect a liquid sample, and includes:

an intermediate cell element having a first cell surface that is formed with a plurality of cell recess portions, and a second cell surface that is opposite to the first cell surface, the intermediate cell element being formed with a plurality of pairs of first and second guiding channels, each pair of which is in fluid communication with a respective one of the cell recess portions and extends to the second cell surface;

a first cell element disposed at the first cell surface of the intermediate cell element and cooperating with the cell recess portions to form a plurality of sensor disposing spaces within which the sensor devices are to be disposed, respectively, each of the cell recess portions being adapted to cooperate with a sample contacting side of the respective one of the sensor devices so as to confine a sample receiving space for receiving the liquid sample; and a second cell element disposed at the second cell surface of the intermediate cell element, formed with an inlet channel in fluid communication with the first guiding channel that extends to a first one of the cell recess portions for introducing the liquid sample into one of the sample receiving spaces, formed with a number of connecting recess portions each fluidly communicating the second guiding channel and the first guiding channel that respectively extend to a corresponding pair of the cell recess portions such that the liquid sample is able to flow in sequence through the sample receiving spaces, and formed with an outlet channel in fluid communication with the second guiding channel that extends to a last one of the cell recess portions for discharging the liquid sample from the flow cell device.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
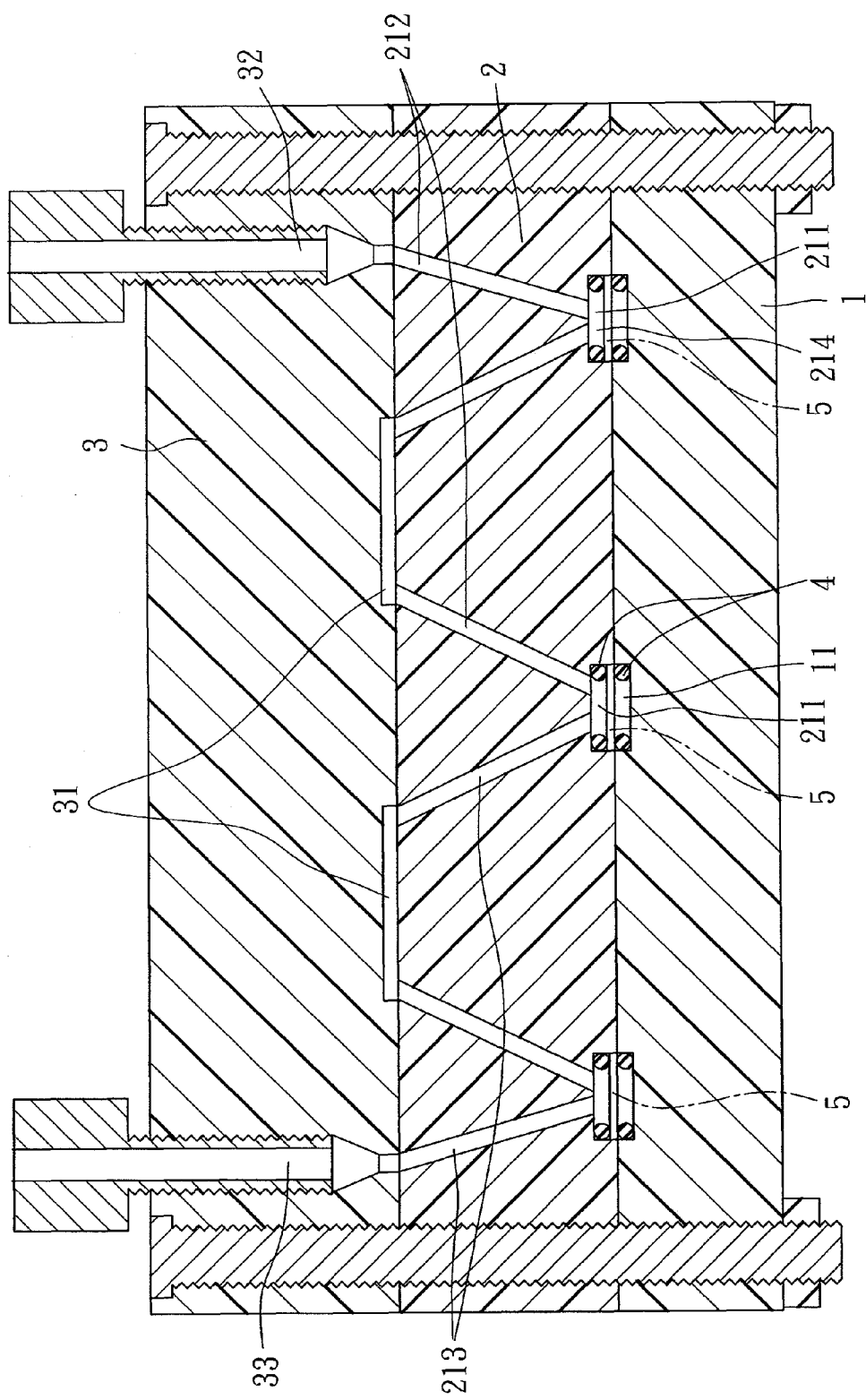
FIG. 1 is a cross-sectional view of the first preferred embodiment of a flow cell device according to the present invention.

Before the present invention is described in greater detail, it should be noted that like elements are denoted by the same reference numerals throughout the disclosure.

Referring to FIG. 1, the first preferred embodiment of a flow cell device according to the present invention is adapted for use with a plurality of sensor devices 5 to detect concentration of a predetermined osteoarthritis biomarker in such as a urine sample. The flow cell device of the first preferred embodiment includes a first cell element 1, an intermediate cell element 2, a second cell element 3, and a plurality of pairs of leak-proofing rings 4. The first cell element 1 and the intermediate cell element 2 are secured to each other through threaded engagement, and the second cell element 3 and the intermediate cell element 2 are secured to each other through threaded engagement. In this embodiment, a plurality of screw bolts are used to fasten the first cell element 1, the intermediate cell element 2, and the second cell element 3 together in a stack.

The intermediate cell element 2 has a first cell surface that is formed with a plurality of cell recess portions 211, and a second cell surface that is opposite and parallel to the first cell surface. The intermediate cell element 2 is formed with a plurality of pairs of first and second guiding channels 212, 213, each pair of which is in fluid communication with a respective one of the cell recess portions 211 and extends to the second cell surface.

The first cell element 1 is disposed at the first cell surface, and has a first surface abutting against the first cell surface and formed with a plurality of recess portions 11 that correspond in position to and cooperate with the cell recess portions 211 to form a plurality of sensor disposing spaces 214 within which the sensor devices 5 are to be disposed, respectively. Each pair of the leak-proofing rings 4 is made of rubber, is disposed in a respective one of the sensor disposing spaces 214, and is adapted to clamp removably the sensor device 5 disposed in the respective one of the sensor disposing spaces 214. The leak-proofing rings 4, together with the first cell element 1 and the intermediate cell element 2, are adapted to cooperate with the sensor devices 5 so as to prevent the liquid sample from leaking between the first cell element 1 and the intermediate cell element 2. Moreover, each of the cell recess portions 211 is adapted to cooperate with a sample contacting side of the respective one of the sensor devices 5 so as to confine a sample receiving space for receiving the liquid sample.

Figure 2:
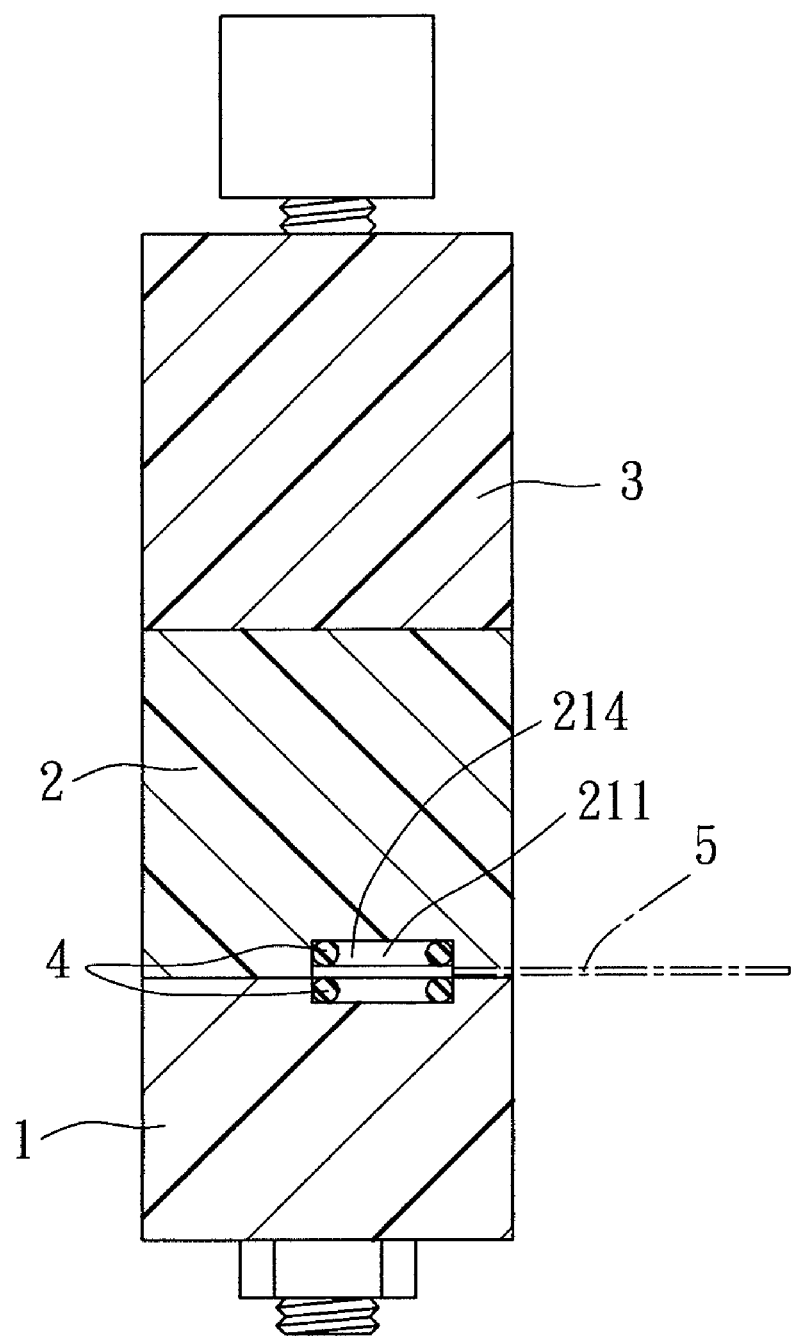
FIG. 2 is a fragmentary cross-sectional view of the flow cell device.

Referring to FIG. 2, each of the sensor devices 5 is operable for detecting concentration of the predetermined biomarker in the urine sample and for generating an electrical signal accordingly, and has an interface portion extending between the intermediate cell element 2 and the first cell element 1 for connecting to such as a computing device for outputting the electrical signal thereto. Since the feature of the invention does not reside in the sensor devices 5, which are known in the art, further details of the same are omitted herein for the sake of brevity.

In this embodiment, each of the first and second guiding channels 212, 213 is a linear guiding channel. Each of the first guiding channels 212 forms a first predetermined angle with the first cell surface of the intermediate cell element 2. Each of the second guiding channels 213 forms a second predetermined angle with the first cell surface of the intermediate cell element 2. For each of the pairs of the first and second guiding channels 212, 213, a first line that extends along the first guiding channel 212 intersects a second line that extends along the second guiding channel 213, and forms a third predetermined angle therewith.

The second cell element 3 is disposed at the second cell surface of the intermediate cell element 2, and is formed with an inlet channel 32, a number of connecting recess portions 31, and an outlet channel 33. The inlet channel 32 is in fluid communication with the first guiding channel 212 that extends to a first one of the cell recess portions 211 for introducing the liquid sample into one of the sample receiving spaces. Each of the connecting recess portions 31 fluidly communicates the second guiding channel 213 and the first guiding channel 212 that respectively extend to a corresponding pair of the cell recess portions 211 such that the liquid sample is able to flow in sequence through the sample receiving spaces. The second cell element 3 has a second surface abutting against the second cell surface of the intermediate cell element 2, with the connecting recess portions 31 being preferably formed on the second surface of the second cell element 3. The outlet channel 33 is in fluid communication with the second guiding channel 213 that extends to a last one of the cell recess portions 211 for discharging the liquid sample from the flow cell device.

It is to be noted that, in this embodiment, each of the connecting recess portions 31 is linear and extends substantially parallel to the second cell surface of the intermediate cell element 2. Furthermore, each of the sensor disposing spaces 214 is substantially centered between projections of a respective pair of the first and second guiding channels 212, 213, that are in fluid communication with the corresponding one of the cell recess portions 211, onto the first cell surface of the intermediate cell element 2.

Moreover, in the present embodiment: the first, intermediate, and second cell elements 1, 2, 3 are disposed in a horizontal position; the first and second cell surfaces of the intermediate cell element 2, the first surface of the first cell element 1, and the second surface of the second cell element 3 are parallel to one another; the first and second guiding channels 212, 213 have equal heights; and the sensor disposing spaces 214 are disposed at a same height; such that the liquid sample has substantially the same pressure in the sample receiving spaces.

However, configurations of the connecting recess portions 31, the first and second guiding channels 212, 213, and the sensor disposing spaces 214 are not limited to such, and may be modified to meet design needs.

It is worth noting that such arrangement of the sensor devices 5 with respect to the first, intermediate, and second cell elements 1, 2, 3 and the pairs of leak-proofing rings 4 ensures substantially uniform distribution of the urine sample over the sample contacting sides of the sensor devices 5, thereby improving precision and reliability of a measurement result thus obtained. In a modification, the sensor devices 5 may be adjusted respectively to measure concentrations of respective biomarkers in a same liquid sample. Adjustment of the sensor devices 5 (i.e., configurations of the circuits of the sensor devices 5) is well known to a skilled artisan, and will not be described hereinafter.

Figure 3:
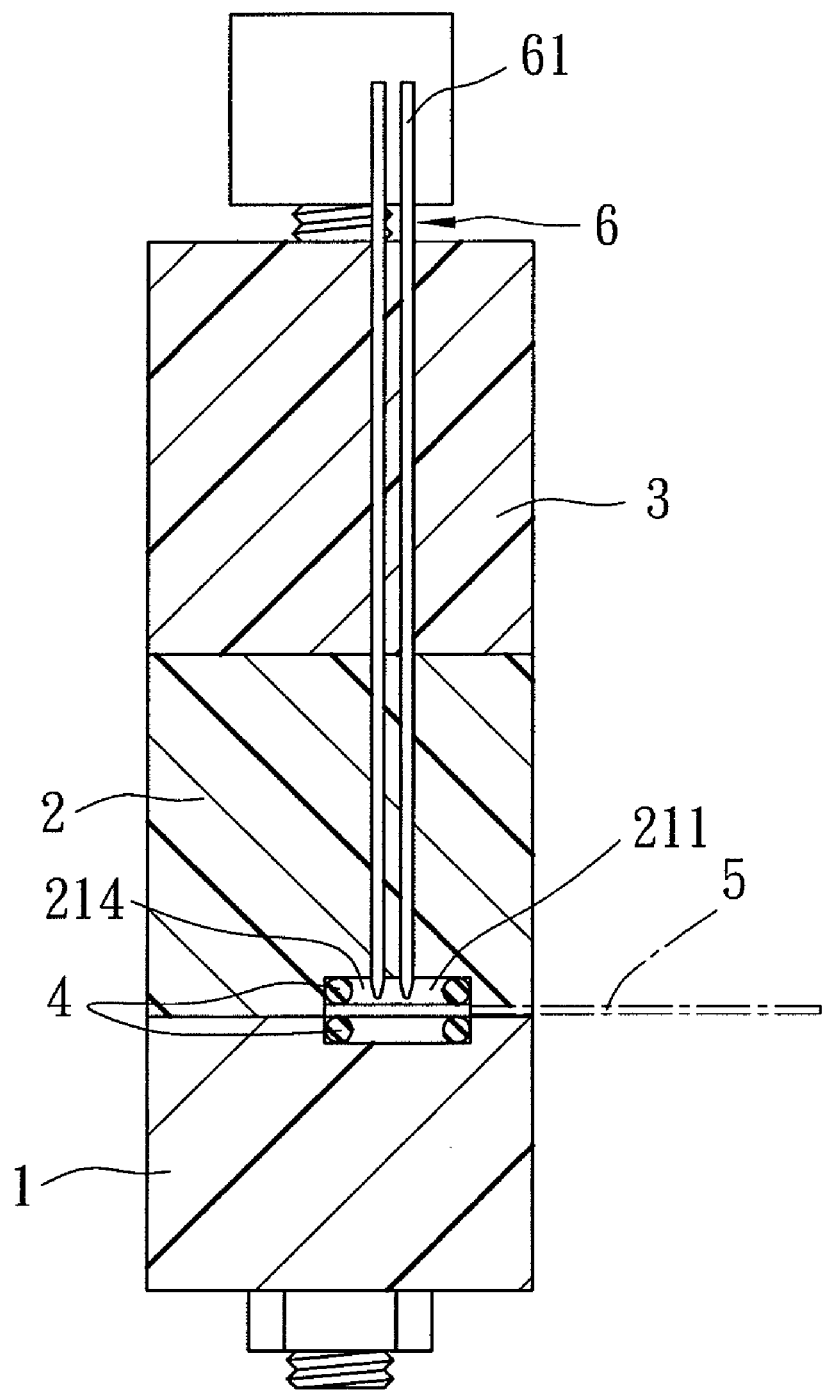
FIG. 3 is a fragmentary cross-sectional view of the second preferred embodiment of a flow cell device according to the present invention.

Referring to FIG. 3, the second preferred embodiment of a flow cell device according to the present invention is similar to the first preferred embodiment, and further includes a set of conductive probe elements 6 including a pair of metallic probes 61. In the second preferred embodiment, the metallic probes 61 are made of gold (Au) and silver (Ag), respectively. The pair of metallic probes 61 extends through the second cell element 3 and the intermediate cell element 2, and extends into one of the sample receiving spaces for electrochemical signal communication with the urine sample in said one of the sample receiving spaces. Subsequently, the sensor device 5 corresponding to said one of the sample receiving spaces detects electrochemical changes in the urine sample and generates the electrical signal accordingly.

In summary, the structure of the flow cell device of this invention ensures that the urine sample flows through each of the sample receiving spaces in sequence at a substantially uniform rate such that measurement results thus obtained have higher precision and reliability.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A flow cell device adapted for use with a plurality of sensor devices to detect a liquid sample, said flow cell device comprising:

an intermediate cell element having a first cell surface that is formed with a plurality of cell recess portions, and a second cell surface that is opposite to said first cell surface, said intermediate cell element being formed with a plurality of pairs of first and second guiding channels, each pair of which is in fluid communication with a respective one of said cell recess portions and extends to said second cell surface;

a first cell element disposed at said first cell surface of said intermediate cell element and cooperating with said cell recess portions to form a plurality of sensor disposing spaces within which the sensor devices are to be disposed, respectively, each of said cell recess portions being adapted to cooperate with a sample contacting side of the respective one of the sensor devices so as to confine a sample receiving space for receiving the liquid sample; and a second cell element disposed at said second cell surface of said intermediate cell element, formed with an inlet channel in fluid communication with said first guiding channel that extends to a first one of said cell recess portions for introducing the liquid sample into one of said sample receiving spaces, formed with a number of connecting recess portions each fluidly communicating said second guiding channel and said first guiding channel that respectively extend to a corresponding pair of said cell recess portions such that the liquid sample is able to flow in sequence through said sample receiving spaces, and formed with an outlet channel in fluid communication with said second guiding channel that extends to a last one of said cell recess portions for discharging the liquid sample from said flow cell device.

2. The flow cell device as claimed in claim 1, wherein each of said first and second guiding channels is a linear guiding channel, each of said first guiding channels forming a first angle with said first cell surface of said intermediate cell element, each of said second guiding channels forming a second angle with said first cell surface of said intermediate cell element, and wherein, for each of said pairs of said first and second guiding channels, a first line that extends along said first guiding channel intersects a second line that extends along said second guiding channel, and forms a third angle therewith.

3. The flow cell device as claimed in claim 2, wherein each of said connecting recess portions is linear and extends parallel to said second cell surface of said intermediate cell element.

4. The flow cell device as claimed in claim 3, wherein each of said sensor disposing spaces is centered between projections of a respective pair of said first and second guiding channels, that are in fluid communication with the corresponding one of said cell recess portions, onto said first cell surface of said intermediate cell element.

5. The flow cell device as claimed in claim 4, wherein said first guiding channels have equal heights, said second guiding channels have equal heights, and said sensor disposing spaces are disposed at a same height such that the liquid sample has the same pressure in said sample receiving spaces.

6. The flow cell device as claimed in claim 1, wherein said first cell element and said intermediate cell element are secured to each other through threaded engagement, and said second cell element and said intermediate cell element are secured to each other through threaded engagement.

7. The flow cell device as claimed in claim 1, wherein said first cell element has a first surface abutting against said first cell surface of said intermediate cell element and formed with a plurality of recess portions that correspond in position to and cooperate with said cell recess portions to form said sensor disposing spaces, respectively.

8. The flow cell device as claimed in claim 1, further comprising a plurality of pairs of leak-proofing rings each pair of which is disposed in a respective one of said sensor disposing spaces and is adapted to clamp removably the sensor device disposed in the respective one of said sensor disposing spaces, said leak-proofing rings, together with said first cell element and said intermediate cell element, being adapted to cooperate with the sensor devices so as to prevent the liquid sample from leaking between said first cell element and said intermediate cell element.

9. The flow cell device as claimed in claim 8, wherein each of said leak-proofing rings is made of rubber.

10. The flow cell device as claimed in claim 1, further comprising a set of conductive probe elements extending through said second cell element and said intermediate cell element, and extending into at least one of said sample receiving spaces for electrochemical signal communication with the liquid sample in said at least one of said sample receiving spaces.

11. The flow cell device as claimed in claim 7, wherein said second cell element has a second surface abutting against said second cell surface of said intermediate cell element, said connecting recess portions being formed on said second surface of said second cell element.

12. The flow cell device as claimed in claim 11, wherein said first and second cell surfaces of said intermediate cell element, said first surface of said first cell element, and said second surface of said second cell element are parallel to one another.

* * * * *